United States Patent [19]
Ko

[11] Patent Number: 4,830,492
[45] Date of Patent: May 16, 1989

[54] GLOW-DISCHARGE LAMP AND ITS APPLICATION

[75] Inventor: Jae B. Ko, Dortmund, Fed. Rep. of Germany

[73] Assignee: Gesellschaft zur Förderung der Spektrochemie und angewandten Spektrochemie e.V., Dortmund, Fed. Rep. of Germany

[21] Appl. No.: 123,158

[22] PCT Filed: Feb. 24, 1987

[86] PCT No.: PCT/DE87/00063
§ 371 Date: Dec. 22, 1987
§ 102(e) Date: Dec. 22, 1987

[87] PCT Pub. No.: WO87/05110
PCT Pub. Date: Aug. 27, 1987

[30] Foreign Application Priority Data
Feb. 24, 1986 [DE] Fed. Rep. of Germany ....... 3605911

[51] Int. Cl.$^4$ .................. H01J 1/88; G01N 21/66
[52] U.S. Cl. .................. 356/313; 313/619; 356/314
[58] Field of Search .......... 356/311, 313, 314; 313/619

[56] References Cited
FOREIGN PATENT DOCUMENTS

| | | |
|---|---|---|
| 2806212 | 8/1978 | Fed. Rep. of Germany . |
| 3213660 | 10/1983 | Fed. Rep. of Germany . |
| 3429765 | 2/1986 | Fed. Rep. of Germany . |
| 58-127150 | 7/1983 | Japan . |

OTHER PUBLICATIONS

Williamson et al. "Glow-Discharge Optical Spectroscopy Measurement of B-, Ge, & Mg-Implanted GaAs" Jour. of Applied Physics 50(12) Dec. 1979 pp. 8019-8024.

*Primary Examiner*—Vincent P. McGraw
*Attorney, Agent, or Firm*—Barnes & Thornburg

[57] ABSTRACT

The present invention relates to a glow-discharge lamp comprising: a chamber body, provided with one or more gas supply and evacuation openings made of insulated material; a gas inner chamber, which expands toward an anode, is bordered on the sides by the inner walls of the chamber body and has a diameter which is largest at approximately the level of the anode and which has its smallest diameter corresponding to the examination sector of the sample to be examined; a sample arranged at the cathode end of the chamber body and with the anode incorporated in the chamber body, whereby the sample preferably is held at zero potential and the anode incorporated in the chamber body and having a passage opening is preferably held at high voltage; an end piece, if necessary, in the form of a window is arranged at the end of the chamber body, wherein at least one window opening (18) is provided in the chamber body (4) at the level of the negative glow light, and the sample (2) seals the inner gas chamber at the cathode end and to provide for the application of said glow-discharge lamp in atom absorption spectroscopy (AAS), optical emission spectroscopy processes (OES), atom fluoresence spectroscopy (AFS) and optogalvanic processes (LEI).

19 Claims, 2 Drawing Sheets

GLOW-DISCHARGE LAMP AND ITS APPLICATION

BACKGROUND OF THE INVENTION

The present invention relates to a glow-discharge lamp made of insulated material provided with at least one gas supply means and evacuation openings means; an anode in said chamber body; a gas inner chamber which expands toward the anode and which is defined by sides of inner walls of the chamber body and whose diameter is largest at approximately the level of the anode and whose smallest diameter corresponds to an examination sector of the sample to be examined; a cathode adjacent one end of the chamber body; a sample placed at the cathode end of the chamber body and an end section in the form of a window means arranged at one end of the chamber body and wherein the glow-discharge lamp is used for atom absorption spectroscopy (AAS), optical emission spectroscopy processes (OES), atom fluoresence spectroscopy (AFS) and optogalvanic process (LEI).

STATE OF THE ART

Glow-discharge lamps have found wide use in the analysis of metals by means of atom emission spectroscopy (AES), in which a conductive sample to be examined is connected to a cathode and the region between the cathode and the anode is filled with a gas capable of glow discharge, preferably an inert gas under low pressure. The glow discharge depends on the relationship between the voltage during conduction, the current and the gas pressure between the cathode and the anode. The radiation of the glow discharge is observed through the customary window situated above the anode and from its spectral analysis inforamtion is gained about the content of specific elements in the sample.

A glow-discharge lamp is known from the German Patent Application 34 29 765, in which a carrier gas passes through an inner gas chamber and a glow discharge is excited by applying voltage between the anode and the cathode. The sample is connected as a part of the cathode, whereby a transparent part of the housing is used for the spectral analysis of the glow-discharge light. The anode is partially embedded in a fixed non-conducting body and has high voltage potential, whereas the sample—as the cathode—has zero potential.

The embedding of the anode in a fixed non-conducting body ensures, in a most simple manner, the short circuit resistancy of the housing. Furthermore, this prior art technique permits applying high voltage to the anode while the cathode is at zero potential, by which means it is possiblee to easily and safely replace the samples. The non-conductive material of the gas chamber also makes it possible that the walls of the discharge chamber rapidly adjust to the temperature in the gas chamber as non-conductive material usually has poor thermal conductive properties. This known arrangement ensures rapid establishment of constant measuring conditions and reproduceable results.

Although the apparatus known from P 34 29 765 is major progress compared to known glow-discharge lamps, nonetheless conventional glow-discharge lamps are only suited for the customary application in atom emission spectroscopy.

BRIEF DESCRIPTION OF THE INVENTION

The object of the present invention is, therefore, to improve known glow-discharge lamps while lowering the detection limit in the atom emission spectropscopy in such a manner that also permits applying other spectroscopic methods, with which excited atoms, like those present in a glow discharge, can be examined.

Said object is carried out in accordance with the present invention and its embodiments as set forth in the appended claims.

A fundamental thought underlying the present invention is the observation of the glow discharge through a side window. By this means, which in contrast to previously known glow-discharge lamps, for the first time provides lateral observation of the glow light, if necessary, following optical excitement from incident radiation. The glow-discharge lamp can thus be used for other spectroscopic processes such as, by way of illustration, atom fluorescence spectroscopy or similar processes. It is also possible to link up a light guide or similar devices to the side window in order to examine the emitted radiation from a distance.

Said side window permits for the first time an opportunity to examine radiation emitted from the sample without excitement rays.

It is advantageous if the chanber body is provided with a first gas supply line opening into the region of the negative glow light; and with an evacuation line arranged above the first gas supply line; and with a second gas supply line, which is arranged between said first gas supply line and below the anode embedded in the chamber body and which, if necessary, can be closed; and with a third gas supply line arranged between the anode and the end section.

Another line can be provided at the end section which can be connected for evacuation as well as for gas supply.

By means of the geometrically balanced low arrangement of the channels for the evacuation and the gas supply lines, is possible to attain even pressure distribution above the sample and therewith a coplanar removal of the samples as is desirable particularly for surface and profile depth analyses.

By means of this different arrangement of the lines, it also possible to adapt the shape of the sample crater to the requirements of the analyses—surface analysis, depth analysis or to specific properties of the material—rough, uneven surfaces with high resolution power or low resolution power.

A replaceable insertion piece can be arranged in the sample-holding cathode piece, which due to its inner opening surrounds the section of the sample, which is exposed to the vacuum or the removal of materials. Said cutout can be regulated in any desired manner by the selection of insertion piece depending on whether the sector of the sample to be examined is small or whether a large surface is to be removed.

Due to the direct dispersion of the sample and the invented arrangement of the window, the reservoir of free atoms can be used for the processes of atom absorbtion spectroscopy, atom fluorescence spectroscopy and LEI (laser enhanced ionisation). The coplanar dispersion of the sample makes it possible to employ the above said processes successfully not only for average analysis, but also for the firt time for surface and depth profile analysis.

BRIEF DESCRIPTION OF THE DRAWING

The present invention is made more apparent using a preferred embodiment with reference to the accompanying drawings, depicting.

DETAILED DESCRIPTION OF THE DRAWINGS

Figure 1:
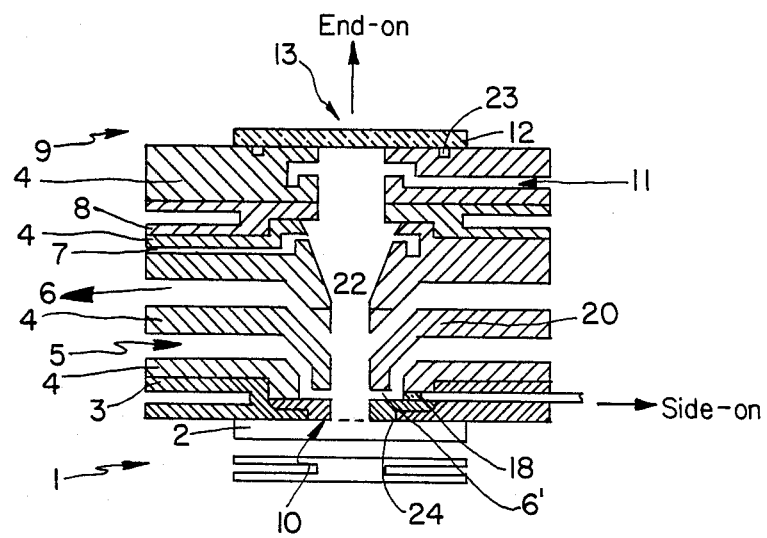
FIG. 1 the essential parts of an invented glow-discharge lamp, cut along the connection line anode-cathode.

As shown in FIG. 1, the invented glow-discharge is provided with a sample 2, which is mounted in a sealing manner onto a cathode piece 3, by means of a seal, by way of illustration a ring seal 24. Said cathode piece joins the chamber body 4, which is made of a non-conducting material, preferably a ceramic material, and which is provided with a first gas supply line 5 ending just above the sample. A first evacuation line 6 is arranged above the first gas supply line and below a second gas supply line 7, preferably having a smaller cross-section than the first gas supply line a anode 8 is embedded in the chamber body 4. A third gas supply line 11 supplies argon above said anode and under the end section 12. All the lines end in a gas inner chamber 22. The chamber body 4 is provided with a passage opening, the gas inner chamber 21, which, in this preferred embodiment, expands truncated conical in shape toward the anode 8, starting at the sample 2. Said anode has an inner opening, which aligns with the axis of said gas inner chamber 21. Said gas inner chamber 21 is closed by an end piece 12, which, by way of illustration, may be a window, and which, if necessary, can be provided with an additional line for the gas supply line or for the evacuation connection, and which is also sealed with O-rings 23 in the embodiment depicted herein.

Furthermore, there is at least one side observation window 18 in the cathode piece, through which the negative glow light developing above the sample in the gas inner chamber 21 can be observed.

If necessary, an additional observation window can be provided, which can be used to introduce radiation, by way of illustration excitement radiation in the UV (ultraviolet) or VIS (visible) range. The introduction of radiation to excite the atoms present in the negative glow light can also ensue via the end window 12 and be obwerved from the side. In a preferred embodiment, a light guide, which permits linking up to a relative distant spectrometer is substituted for the observation window 18.

Figure 2:
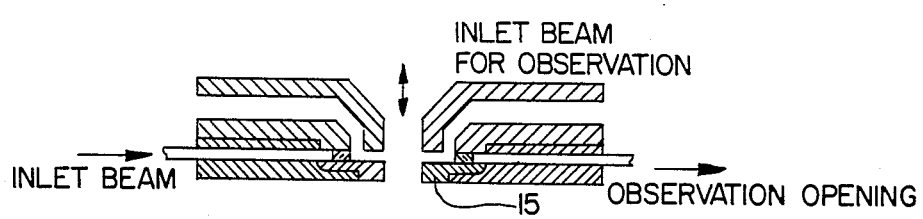
FIG. 2 the sample side of the glow-discharge lamp of FIG. 1, cut along the evacuation line.

As illustrated in FIG. 2, even an aligned arrangement of an opening forobservation and for introducing radiation can be provided.

Preferably the sample's surface area, which is to be exposed to the detection process, is confined by an insertion piece 15, as shown in FIG. 2, whereby it is possible to modify the inner opening of the sample piece according to the process employed or the type of analysis results desired.

Figure 3:
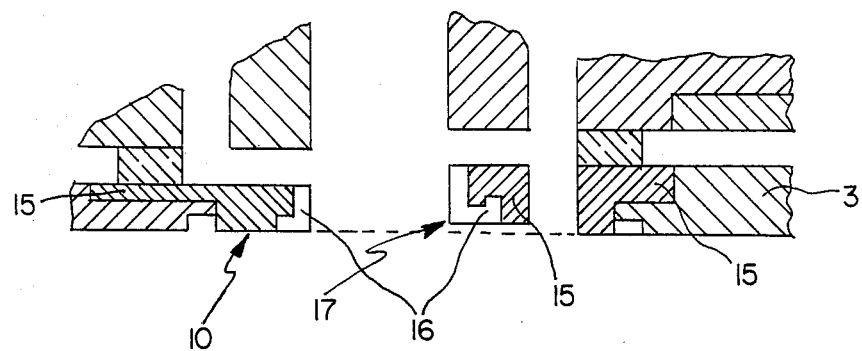
FIG. 3 two enlarged sections of possible preferred embodiments of the sample region of an invented glow-discharge lamp and FIG. 4 a further preferred embodiment of the invented glow-discharge lamp in the region of the end section, with a shielded anode.

FIG. 3 depicts enlarged the sample region of two embodiments of the invented glow-discharge lamp (left and right differing), whereby the insertion piece 15 is provided with an opening 17 for a mode of operation, in which an additional divider piece 16 is provided, which is designed in such a manner that it is replaceable. Said divider piece 16 is provided with the opening 17, through which a part or all of the carrier gas, depending on the purpose of the operation, can pass into the chamber, whereby the distance between the front surface of the insertion piece 15 is 0.01 to 0.5 mm, preferably less than 0.2, before the sample.

Figure 4:
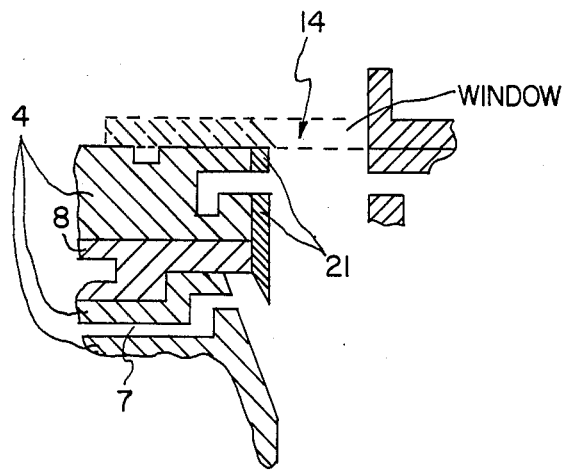

In a further preferred embodiment of the invented glow-discharge lamp, as illustrated in FIG. 4, the anode 8 is shielded from the gas inner chamber by a parition wall 21. The mode of procedure with said shielded anode is advantageous in some preferred applications of the invented glow-discharge lamp. Preferably no metal or conducting parts on the anode 8 or sample 2 should border the gas inner chamber.

Said entire, described chamber is usually shielded by a thin metal sheet having zero potential, which is not depicted in the accompanying figures for reason of lucidity.

Preferred modes of operation of the invented glow-discharge lamp are described in the following with different samples.

Normally, the invented glow-discharge lamp is operated at high voltage (sample as cathode has a zero potential and the anode has a high voltage potential) by filling the openings 5 and 11 with argon and evacuating at opening 6.

There are samples, as by way of illustration, purest aluminum, or also very rough samples, with which it is, under circumstances, advantageous to enter in a carrier gas via openings 11 and 17.

For particularly high requirements, it may be useful, if the inert gas supply lines 5,7, and 17 are closed and inert gas only enters through the opening 11, while evacuating via opening 6.

The latter mode of operation is particularly suited for samples of aluminum silicon alloys, which decompose with difficulty and conduct poorly as is usually the case with high-melting point materials with high cohesive energy.

If attaining a low decomposition rate of the sample is desired, it is favorable to close the inert gas supply line 11 and line 17 and only enter inertgas via the lines 5 and 7, while evacuating via opening 6.

It can be favorable for other analytic processes to evacuate via opening 17 and enter inert gas via openings 5, 7, or 11, whereas, if necessary, additional evacuating can be done via opening 6.

By means of the invented arrangement of a glow-discharge lamp, it is possible or the first time not only to measure end-on (downwardly) but also side-on, (at the side) whereby the negative glow light develops at a distance of 0.5 to 20 mm above the sample. The openings 5 in the chamber body are provided at plasma level.

By means of the radiation window 18 at the same level as the plasma, it is possible to observe this process closely and, if necessary, to excite the ions/atoms present in the glow-discharge with radiation and to observe their emission spectra.

In atom absorption spectroscopy or atom fluorescence spectroscopy, the known light sources may be employed as primary sources of radiation in connetion with the invented glow-discharge lamp. In particular, light sources may be used which emit light with narrow line width and high coherence. In AAS and AFS, the line width of the light emitted by the light source is typically one dimension smaller than the width of the absorption line: the line width of the light from the light source may be between 5 and 500 MHz, preferably between 10 and 50 MHz. In this connection, semiconductor lasers of variable frequency and stable temperature are preferably employed.

While I have shown and described only plural embodiments in accordance with the present invention, it is understood that the same is not limited thereto but is susceptible to numerous changes and modifications as known to one having ordinary skill in the art, and I therefore do not wish to be limited to the details shown and described herein, but intend to cover all such modifications as are encompassed by the scope of the appended claims.

The present invention is described herein using preferred embodiments without the intention of limiting the scope of the overall inventive idea. In any case, the invented glow-discharge lamp permits for the first time to raise the effectiveness of the analysis to a previously unknown degree by changing the height of the radiation direction above the sample and thereby the relevant discharge layer. By means of the invented arrangement, it is possible to employ gas discharges at lower pressure not only for optical emission spectroscopic process (OES), but rather also for other time-tested process such as atom absorption (AAS), atom fluorescence spectroscopy and the optogalvanic process (LEI) for analyses. In OES, the invented glow-discharge lamp lowers the limits for the detection of traces of elements. By means of the invented arrangement, it is possible, for the first time, to use glow-discharge lamps for other processes besides OES.

As part of the overall inventive idea, a side window opening is provided—naturally there are unlimited possible modifications: by way of illustration, the sample has high voltage potential.

What I claim is:

1. A glow-discharge lamp comprising a chamber body made of insulated material and provided with at least one gas supply means and evacuation openings means; an anode in said chamber body; a gas inner chamber which expands toward the anode and which is defined by sides of inner walls of the chamber body and whose diameter is largest at approximately the level of the anode and whose smallest diameter corresponds to an examination sector of the sample to be examined; a cathode adjacent one end of the chamber body; and a sample placed at the cathode end of the chamber body and an end section in the form of a window means arranged at one end of the chamber body; and
wherein at least one window opening is provided in the chamber body at the level of a negative glow light, and wherein the sample seals said inner gas chamber at the cathode end.

2. A glow-discharge lamp according to claim 1, wherein said at least one gas supply means comprises a first gas supply line, which is arranged said near sample and which can be closed; said at least one evacuation means comprising a first evacuation line which is arranged above the first gas supply line in said chamber body; said at least one gas supplying means also comprises a second gas supply line which is arranged between said first gas supply line and below the anode in said chamber body and which can be closed; said at least one gas supplying means also comprising a third gas supply line, which is arranged between said anode and the end section; and which can be closed.

3. A glow-discharge lamp according to claim 1 wherein said end section is provided with a connection line for evacuation or gas supply and which can be closed.

4. A glow-discharge lamp according to claim 1 wherein said sample is arranged adjacent said cathode.

5. A glow-discharge lamp according to claim 4, wherein a replaceable insertion piece made of non-conducting material having an inner opening corresponding to an examination sector of the sample is arranged in a passage opening in said cathode, whereby the inner opening of said insertion piece can have various configurations.

6. A glow-discharge lamp according to claim 1, wherein said anode is shielded by a partition wall from said gas inner chamber.

7. A glow-discharge lamp according to claim 5, wherein a divider piece made of non-conducting material and having a gas supply line opening is inserted in said insertion piece (15).

8. A glow-discharge lamp according to claim 1, wherein the sample has zero potential and the anode has a passage opening incorporated in the chamber body and has a high voltage.

9. A glow-discharge lamp according to claim 2 wherein said end section is provided with a connection line for evacuation or gas supply and which can be closed.

10. A glow-discharge lamp according to claim 2 wherein said sample is arranged adjacent said cathode.

11. A glow-discharge lamp according to claim 3 wherein said sample is arranged adjacent said cathode.

12. A glow-discharge lamp according to claim 10, wherein a replaceable insertion piece made of non-conducting material having an inner opening corresponding to an examination sector of the sample is arranged in a passage opening in said cathode, whereby the inner opening of said insertion piece can have various configurations.

13. A glow-discharge lamp according to claim 11, wherein a replaceable insertion piece made of non-conducting material having an inner opening corresponding to an examination sector of the sample is arranged in a passage opening in said cathode, whereby the inner opening of said insertion piece can have various configurations.

14. A glow-discharge lamp according to claim 2, wherein said anode is shielded by a partition wall from said gas inner chamber.

15. A glow-discharge lamp according to claim 3, wherein said anode is shielded by a partition wall from said gas inner chamber.

16. A glow-discharge lamp according to claim 12, wherein a divider piece made of non-conducting material and having a gas supply line opening is inserted in said insertion piece.

17. A glow-discharge lamp according to claim 13, wherein a divider piece made of non-conducting material and having a gas supply line opening is inserted in said insertion piece.

18. A glow-discharge lamp according to claim 2, wherein the sample has zero potential and the anode has a passage opening and incorporated in the chamber body and has a high voltage.

19. A method of using the glow-discharge lamp of claim 1 wherein the glow discharge lamp is used for at least one of atom absorption spectroscopy (AAS), optical emission spectroscopy processes (OES), atom fluoresence spectroscopy (AFS) and optogalvanic processes (LEI).

* * * * *